United States Patent
Levings et al.

(10) Patent No.: US 6,746,670 B2
(45) Date of Patent: Jun. 8, 2004

(54) REGULATORY T CELLS; METHODS

(75) Inventors: Megan K. Levings, Milan (IT); Rene de Waal Malefyt, Sunnyvale, CA (US); Maria Grazia Roncarolo, Milan (IT)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/929,863

(22) Filed: Aug. 14, 2001

(65) Prior Publication Data

US 2002/0034500 A1 Mar. 21, 2002

Related U.S. Application Data

(60) Provisional application No. 60/225,502, filed on Aug. 15, 2000.

(51) Int. Cl.[7] .................. A61K 38/21; A61K 45/00; A61K 39/00; A01N 1/02
(52) U.S. Cl. ................. 424/85.7; 424/85.2; 424/198.1; 435/2
(58) Field of Search .............................. 424/85.8, 85.2, 424/198.1; 433/2

(56) References Cited

U.S. PATENT DOCUMENTS 6,346,243 B1 * 2/2002 Brod .......................... 424/85.4

FOREIGN PATENT DOCUMENTS

WO    WO 88/03411    * 5/1988

OTHER PUBLICATIONS

Lin et al., J. Exp. Med., 1998, vol. 187, pp. 79–87.*
Avice et al., J. Immunol., 1998, vol. 161, pp. 3408–3415.*
Rosa Bacchetta, et al., *J Exp Med.*, 179(2):493–502, Feb. 1, 1994. "High levels of interleukin 10 production in vivo are associated with tolerance in SCID patients transplanted with HLA mismatched hematopoietic stem cells".
Frank Bridoux, et al., *J Exp Med.*, 185(10):1769–75, May 19, 1997. "Transforming growth factor beta (TGF–beta)–dependent inhibition of T helper cell 2 (Th2)–induced autoimmunity by self–major histocompatibility complex (MHC) class II–specific, regulatory CD4(+) T cell lines".
Jan Buer, et al., *J Exp Med.*, 187(2):177–8, Jan. 19, 1998. "Interleukin 10 secretion and impaired effector function of major histocompatibility complex class ll–restricted T cells anergized in vivo".
Marina Cella, et al., *Nature Medicine*, 5(8):919–23, Aug. 1999. "Plasmacytoid monocytes migrate to inflamed lymph nodes and produce large amounts of type l interferon".
Nitya G. Chakraborty, et al., *J Immunol.*, 162(9):5576–83, May 1, 1999. "Emergence of regulatory CD4+ T cell response to repetitive stimulation with antigen–presenting cells in vitro: implications in designing antigen–presenting cell–based tumor vaccines".
Herve Groux, et al., *J Immunol.*, 160(7):3188–93, Apr. 1, 1999. "Inhibitory and stimulatory effects of IL–10 on human CD8+ T cells".
Ui Yen Khoo, et al., *J Immunol.*, 158(8):3626–34, Apr. 15, 1999. "CD4+ T cell down–regulation in human intestinal mucosa: evidence for intestinal tolerance to luminal bacterial antigens".
Philippa Marrack, et al., *J Exp Med.*, 189(3):521–30, Feb. 1, 1999. Type I interferons keep activated T cells alive.
Sampsa Matikainen, et al. *Blood*, 93(6):1980–91, Mar. 15, 1999. "Interferon–alpha activates multiple STAT proteins and upregulates proliferation–associated IL–2Ralpha, c–myc, and pim–1 genes in human T cells".
Bradford L. McRae, et al., *J Immunol.* 160(9):4298–304, May 1, 1998. "Type I IFNs inhibit human dendritic cell IL–12 production and Th1 cell development".
Carla Miller, et al., *J Exp Med.*, 190(1):53–64, Jul. 5, 1999. "Anergy and cytokine–mediated suppression as distinct superantigen–induced tolerance mechanisms in vivo".
Fiona Powrie, et al., *J Exp Med.*, 183(6):2669–74, Jun. 1, 1996. "A critical role for transforming growth factor–beta but not interleukin 4 in the suppression of T helper type 1–mediated colitis by CD45RB(low) CD4+ T cells".
Lars Rogge & Francesco Sinigaglia, *Chem Immunol.*, 68:38–53, 1997. "Early events controlling T–helper cell differentiation: the role of the IL–12 receptor".
Lars Rogge, et al., *J Immunol.*, 161(12):6567–74, Dec. 15, 1998. "The role of Stat4 in species–specific regulation of Th cell development by type I IFNs".
Robert A. Seder, et al., *J Immunol.*, 160(12):5719–28, Jun. 15, 1998. "Factors involved in the differentiation of TGF–beta–producing cells from naive CD4+ T cells: IL–4 and IFN–gamma have opposing effects, while TGF–beta positively regulates its own production".
Frederick P. Siegal, et al., *Science*, 284(5421):1835–7, Jun. 11, 1999. The natura of the principal type 1 interferon–producing cells in human blood.
Thierry Sornasse, et al., *J Exp Med.*, 184(2):473–83, Aug. 1, 1996. "Differentiation and stability of 1 helper 1 and 2 cells derived from naive human neonatal CD4+ T cells, analyzed at the single–cell level".
Anette Sundstedt, et al., *J Immunol.*, 159(1):180–6, Jan. 1, 1997. "Immunoregulatory role of IL–10 during superantigen–induced hyporesponsiveness in vivo".

* cited by examiner

*Primary Examiner*—Lorraine Spector
*Assistant Examiner*—Janet L. Andres
(74) *Attorney, Agent, or Firm*—Edwin P. Ching; Tom Brody

(57) ABSTRACT

Methods for increasing yields of Tr1 cells, useful, e.g., in transplantation contexts. Use of interferon and IL-15 are described.

12 Claims, No Drawings

REGULATORY T CELLS; METHODS

The application claims benefit of U.S. provisional patent application No. 60/225,502, filed Aug. 15, 2000.

FIELD OF THE INVENTION

The invention relates generally to methods of preparing immune cells in a mammal. These cells, designated Tr1 cells, are a subset of regulatory T cells which can suppress antigen specific immune responses.

BACKGROUND

Interleukin-10 is a cytokine which was originally characterized by its activities in suppressing production of Th1 cytokines. See, e.g., de Vries and de Waal Malefyt (eds. 1995) *Interleukin*-10 Landes Co., Austin, Tex.; etc.

Suppression of immunological function finds utility in many different contexts. See, e.g., Paul (ed. 1998) *Fundamental Immunology* 4th ed., Raven Press, NY. In particular, allogeneic immunity is important in a transplantation context, due largely to its extraordinary strength. As organ and tissue transplants become more common in medical contexts, the ability to minimize problems from tissue rejection exhibit larger economic advantages. In addition, means to minimize autoimmune conditions, to block certain responses to particulate antigens, e.g., bacterial and parasitic, and to minimize reaction to certain soluble antigens, both protein and allergens, will be significant advances for therapeutic purposes.

The lack of fully effective therapeutics to minimize or eliminate tissue rejection, graft vs. host disease, or these other immunological responses leads to many problems. The present invention addresses and provides solutions to many of these problems.

SUMMARY OF THE INVENTION

The present invention is based, in part, upon the surprising discovery of methods to improve the efficiency or yields of making Tr1 cell populations. The present invention provides methods comprising contacting T cell precursor with an appropriate amount of interferon-α (IFN-α), wherein the contacting induces differentiation to a Tr1 cell. In certain embodiments, the Tr1 cell is characterized by CD4 expression, high level of IL-10 production, significant levels of TGF-β or IFN-γ production, and/or little or no IL-4 or IL-2. In preferred embodiments, the high level of IL-10 production is at least 6000 pg in 1 ml for $10^6$ cells in 48 h; the significant level of TGF-β production is at least 600 pg in 1 ml for $10^6$ cells in 48 h; the significant level of IFN-γ production is at least 1000 pg in 1 ml for $10^6$ cells in 48 h; the little or no IL-4 is less than 200 pg in 1 ml for $10^6$ cell in 48 h; and/or the little or no IL-2 is less than 200 pg in 1 ml for $10^6$ cell in 48 h. In other embodiments, the Tr1 cell: has a reduced proliferative potential in response to polyclonal activation; and/or suppresses response to alloantigens by responder T cells.

In yet other methods, the Tr1 cells suppress antigen-specific activation of naive autologous T cells; the suppressed response to alloantigens is mediated by IL-10 and/or TGF-β; the T cell precursors are: CD4+; and/or cord blood leucocytes, including a peripheral blood T cell. In many embodiments, the contacting is in combination with an appropriate amount of IL-10 and/or with an antigen. Preferred antigens used in the method will be alloantigens. Methods are also provided wherein the Tr1 cells are further proliferated in IL-15 or the Tr1 cells are further tested for antigen specificity.

In another embodiment, the invention provides methods for increasing the number of Tr1 cells, comprising contacting cells with IL-15 and allowing growth, thereby resulting in an increase in the number of the Tr1 cells. In certain embodiments, the allowing growth is culturing for at least 2 days; the increase is at least 3 fold; or the cells are Tr1 cells. Often, the contacting is in a tissue culture plate; or the Tr1 cells are specifically anergic to alloantigen.

DETAILED DESCRIPTION OF THE INVENTION

OUTLINE

I. General
II. Tr1 Cells
   A. IFN-α and Differentiation
   B. Properties
   C. IL-15 Cultures
III. Uses

I. General

T-regulatory cells have an important role in peripheral tolerance, but it has been difficult to isolate cells with suppressive activity in vitro and to define their mechanism of action. A CD4+ T-regulatory cell subset has been described which is able to suppress antigen-specific immune responses in vitro and in vivo. See, e.g., U.S. Pat. No. 6,277,635; and Groux, et al. (1997) *Nature* 389:737–742; each of which is incorporated herein by reference. Type 1 T-regulatory (Tr1) cells are defined, in part, by their unique cytokine profile: they produce high levels of IL-10, significant levels of TGF-β and IFN-γ, but no IL-4 or IL-2. Herein, it is investigated whether in vitro differentiation of human Tr1 cells from naive CD4+ T cells is regulated by cytokines. It is shown that in cord blood T cells, IFN-α induces differentiation of a population of cells with a Tr1-like profile of cytokine production. In contrast, with peripheral blood T cells, both exogenous IL-10 and IFN-α were required for differentiation of Tr1 cells. Cultures with Tr1 cells had a reduced proliferative capacity in response to polyclonal activation, and a suppressed response to alloantigens. Suppression of the alloantigen response was mediated in part by IL-10 and TGF-β. The present invention is based, in part, on the definition of conditions for in vitro differentiation of human Tr1 cells. This will facilitate further characterization of this unique T-cell subset and enable their clinical use as cellular therapy to induce tolerance to foreign proteins, e.g., alloantigens.

The qualitative characteristics of immune responses are regulated by T-cell subsets through their production of distinctive cytokines. Two well-characterized T-cell subsets are the Th1 cells that, via production of IFN-γ, promote cell-mediated responses against bacteria, and Th2 cells that, by producing IL-4, IL-5, and IL-13, promote antibody production, and the anti-parasite mast cell and eosinophil responses. Abbas, et al. (1996) *Nature* 383:787–793. Both T helper subsets originate from a naive T-cell precursor, whose differentiation is influenced by both the manner and the environment in which it is initially stimulated. Variables known to influence the development of T-cell subsets include the affinity of the TCR for antigen (Constant and Bottomly (1997) *Ann. Rev. Immunol.* 15:297–322), the duration of the interaction between TCR and antigen (lezzi, et al. (1999) *Eur. J. Immunol.* 29:4092–4101), and differential co-stimulation by APCs (McAdam, et al. (1998) *Immunol.*

Rev. 165:231–247). However, the best defined differentiating factors are the cytokines present upon T cell activation. Thus, it is clear that the presence of IL-12 during priming favors the development of Th1 cells, whereas IL-4 favors the development of Th2 cells. O'Garra (1998) *Immunity* 8:275–283; Romagnani (1991) *Immunol. Today* 12:256–257; and Romagnani (1997) *Immunol. Today* 18:263–266.

Evidence has been provided for the existence of a CD4$^+$ T cell subset which has a profile of cytokine production distinctive from classical Th1 or Th2 cells. Groux, et al. (1997) *Nature* 389:737–742. Activation of human or mouse CD4$^+$ T cells in the presence of IL-10 resulted in T-cell clones which produced high levels of IL-10, significant amounts of IFN-γ, TGF-β, and IL-5, but no IL-4 or IL-2. Groux, et al. (1997) *Nature* 389:737–742. In addition, kinetic studies demonstrated that these T-cell clones produced IL-10 much more rapidly than did Th1 or Th2 clones. Bacchetta, et al. (1994) *J. Exp. Med.* 179:493–502. Importantly, antigen-specific activation of naive autologous T cells was blocked by these T cell clones, and this inhibition was partially mediated by IL-10 and TGF-β. This novel CD4$^+$ T-cell subset has been designated T-regulatory type 1 (Tr1) cells. Both human and mouse Tr1 clones display a low proliferative capacity under standard culture conditions, and this is likely a major reason why Tr1 cells had not been previously isolated.

In addition, in a murine model of inflammatory bowel disease (IBD) in SCID mice, co-transfer of Tr1 clones together with pathogenic CD4$^+$CD45RB$^{hi}$ T cells prevented the induction of disease. Groux, et al. (1997) *Nature* 389:737–742. Prevention of IBD was only observed in mice that were administered the antigen recognized by Tr1 cells, demonstrating that Tr1 cells must be activated in vivo via the TCR to exert their regulatory effects. Donor-derived T cells which are specific for host alloantigens which possessed a Tr1-profile of cytokine production have been isolated from tolerant SCID patients who had been reconstituted with HLA-mismatched stem cells. Bacchetta, et al. (1994) *J. Exp. Med.* 179:493–502; Bacchetta, et al. (1993) *J. Clin. Invest.* 91:1067–1078; and Bacchetta, et al. (1990) *J. Immunol.* 144:902–908. Together, these data support the hypothesis that Tr1 cells function as regulatory cells in vivo.

Other investigators have also reported the presence of (a) novel subset(s) of CD4$^+$ T cells that secrete high levels of IL-10 and/or TGF-β, and that have regulatory activities similar to those we have described. Notably, in most cases, these regulatory cells appear to arise following repeated antigen stimulation either in vitro or in vivo. Buer, et al. (1998) *J. Exp. Med.* 187:177–183 reported that IL-10-producing T cells are generated in vivo following repeated antigen stimulation, and that although these T cells were unable to proliferate in vitro, they could nevertheless produce high levels of IL-10 and regulate immune responses to influenza hemagglutinin. Similarly, repetitive in vitro stimulation with antigen-loaded APC (Chakraborty, et al. (1999) *J. Immunol.* 162:5576–5583) or in vivo stimulation with superantigen (Miller, et al. (1999) *J. Exp. Med.* 190:53–64; and Sundstedt, et al. (1997) *J. Immunol.* 158:180–186), lead to the emergence of CD4$^+$ T cells that suppressed naive T-cell responses via an IL-10-dependent mechanism. A number of investigators have also documented the presence of antigen-specific regulatory CD4$^+$ T cells that, via a TGF-β-dependent mechanism, can prevent T cell-mediated diseases. Chen, et al. (1994) *Science* 265:1237–1240; Powrie, et al. (1996) *J. Exp. Med.* 183:2669–2674; Han, et al. (1996) *J. Autoimmun.* 9:331–339; Bridoux, et al. (1997) *J. Exp. Med.* 185:1769–1775; and Khoo, et al. (1997) *J. Immunol.* 158:3626–3634. Thus, there is now a large body of evidence that supports the notion that clonal suppression mediated by regulatory cells which produce suppressive cytokines is an important mechanism of peripheral tolerance. This is in addition to the well recognized mechanisms of clonal deletion and clonal anergy.

In order to better understand how Tr1 cells arise in vivo, it is important to define conditions to differentiate this unique T-cell subset in vitro. Culture conditions were developed to test the ability of IL-10, in combination with other immunoregulatory cytokines, to induce the differentiation of polarized populations of CD4$^+$ T cells that produced IL-10 and IFN-γ, no IL-4 or IL-2, and displayed immunoregulatory properties.

II. Tr1 Cell Differentiation

IL-10 alone, or in combination with TGFβ$_2$, is not sufficient to induce the in vitro differentiation of Tr1 cells. Based on the observations that addition of IL-10 to primary MLRs increased the frequency of Tr1 clones (Groux, et al. (1997) *Nature* 389:737–742), in vitro culture conditions in the absence of APCs were established to determine if exogenous IL-10 alone was sufficient to induce their differentiation. These studies were initiated with cord blood lymphocytes since these cells have an intrinsic ability to produce high levels of IL-10. de La Selle, et al. (1998) *Blood* 92:3968–3975. In addition, CD4$^+$ cord blood T cells can be efficiently differentiated into polarized populations of Th1 or Th2 cells following activation with anti-CD3 antibodies cross-linked onto CD32$^+$ mouse L-cells in the presence of IL-12 or IL-4 respectively. Sornasse, et al. (1996) *J. Exp. Med.* 184:473–483. Results showed that CD4$^+$ cord blood T cells activated in the presence of IL-10 did not contain a significant population of cells that displayed a Tr1 phenotype (IL-10$^+$, IL-4$^-$, IFN-γ$^+$, IL-2$^+$). Rather, T cells activated in the presence of IL-10 displayed a profile of cytokine production more similar to Th2 cells, and produced proportionately more IL-4 than IFN-γ.

Since Tr1 cells also produce TGF-β, and TGF-β has previously been reported to positively regulate its own production (Seder, et al. (1998) *J. Immunol.* 160:5719–5728), it was reasoned that this cytokine may also be necessary for the differentiation of Tr1 cells. Moreover, in murine cells both exogenous IL-10 and TGF-β$_2$ are required for induction of antigen-specific anergy in vitro (Zeller, et al. (1999) *J. Immunol.* 163:3684–3691). The profile of cytokine production of CD4$^+$ cord blood T cells activated in the presence of IL-10 and/or TGF-β$_2$ was thus analyzed. Activation in the presence of IL-10 and/or TGFβ$_2$ did not result in differentiation of a population of polarized cells. Rather, addition of TGFβ$_2$ resulted in a general suppression of cytokine production. These results are consistent with previous reports that TGF-β strongly inhibits the production of IL-4 and, to a lesser extent, inhibits that of IL-2 and IFN-γ. Swain, et al. (1991) *J. Immunol.* 147:2991–3000; and Demeure, et al. (1994) *J. Immunol.* 152:4775–4782.

CD4$^+$ T cells primed in the presence of IL-10 and IFN-α differentiate into Tr1 cells. It has been previously shown that CD4$^+$ T cells activated by anti-CD3 cross-linked to CD32$^+$ L-cells or in vitro-differentiated dendritic cells, in the presence of IFN-α, produced high levels of IL-10. Demeure, et al. (1994) *J. Immunol.* 152:4775–4782; and McRae, et al. (1998) *J. Immunol.* 160:4298–4304. Accordingly, the effects of IL-10 and IFN-α on the differentiation of CD4$^+$ cord blood T cells were investigated. Activation in the presence of IL-10 and IFN-α resulted in the differentiation of a significant population of T cells with a profile of cytokine production that was distinct from that of classical Th1 or Th2 cells, and similar to that of Tr1 cells. CD4+ cord blood T cells primed in the presence of IL-10 and IFN-α consistently differentiated into a population of cells that produced IL-10, and, in comparison to the Th1 and Th2 cultures, significantly lower numbers of cells producing IL-2 or IL-4. Cultures differentiated in IL-10 and IFN-α contained more IFN-γ-producing cells than Th2 cultures, but fewer than Th1 cultures. In addition, approximately 50% of IL-10-positive cells were also positive for IFN-γ. Addition of neutralizing anti-IL-4 and/or anti-IL-12 antibodies (which inhibit differentiation of Th1 or Th2 cells, respectively) during priming in the presence of IL-10 and IFN-α did not significantly alter this profile of cytokine production.

It is possible that the differentiation of Tr1 cells is influenced by unknown cell-surface or soluble proteins expressed by the murine L-cells used. In order to establish that the cytokine effects were direct, whether IL-10 and IFN-α could promote the differentiation of Tr1 cells from CD4+ cord blood T cells activated by anti-CD3 immobilized on plastic was determined. Following two rounds of stimulation with immobilized anti-CD3, polarized T cell populations were obtained that displayed profiles of cytokine production similar to those obtained when the cells were activated by anti-CD3 cross-linked to CD32+CD80+CD58+ L-cells. These data show that IL-10 and IFN-α act directly on T cells to induce differentiation of Tr1 cells.

CD4+ cord blood T cells activated in the presence of IL-10 and IFN-α are impaired in their response to polyclonal activation and alloantigens. In addition to their profile of cytokine production, defining characteristics of Tr1 cells include their intrinsic low proliferative capacity and their ability to suppress the antigen-specific proliferation of bystander non-Tr1 cells. Groux, et al. (1997) *Nature* 389:737–742; and Bacchetta, et al. (1994) *J. Exp. Med.* 179:493–502. The proliferative capacity of T cells differentiated in the presence of IL-10 and IFN-α were investigated. In comparison to control cultures, cultures containing Tr1 cells displayed a reduced proliferative response to polyclonal activation by anti-CD3 and anti-CD28 antibodies. Tr1 cultures exhibited reduction in $^3$H-thymidine uptake compared to the Th2 control.

In parallel, the proliferative responses of polarized T cells in primary MLRs were tested. Despite the fact that cells differentiated in IL-10 and IFN-α proliferated in response to polyclonal activation (albeit less than Th1 and Th2 controls), they failed to proliferate significantly in response to alloantigens. This profound suppression in primary MLRs suggests that, even though cultures differentiated in IL-10 and IFN-α are not pure Tr1 cells, that nevertheless the Tr1 cells that are present in the cultures are able to suppress antigen-specific responses of bystander, non-Tr1 cells. Importantly, addition of neutralizing anti-IL-10 and/or anti-TGF-β antibodies was able to partially restore proliferation in response to alloantigens. This suggests that at least part of the suppression in the response to alloantigens is mediated by IL-10 and TGF-β. Thus, IL-10 and IFN-α induce the differentiation of a population of T cells that display not only a Tr1-like profile of cytokine production, but also the biological characteristics of regulatory cells.

The relative roles of exogenous IL-10 and IFN-α were compared in differentiation of Tr1 cells from cord blood T cells. Surprisingly, addition of IFN-α alone was sufficient to induce the differentiation of a population of cells with a Tr1-profile of cytokine production. IFN-α alone was sufficient to differentiate a population of cells with a reduced capacity to proliferate following polyclonal activation or stimulation with alloantigens. Addition of exogenous IL-10 did not significantly alter these IFN-α-induced changes.

Cord blood T cells have an intrinsic ability to produce high levels of autocrine IL-10 in comparison to peripheral blood T cells. de La Selle, et al. (1998) *Blood* 92:3968–3975. Following two rounds of stimulation in the absence of polarizing cytokines, and analysis by intracytoplasmic staining, approximately 6% of cord blood T cells were positive for IL-10. In contrast, stimulation of peripheral blood T cells, in the absence of polarizing cytokines, resulted in only 1% of IL-10-positive cells. Addition of neutralizing anti-IL-10 antibodies to cord blood T cells decreased the percentages of IL-10-positive cells to numbers equivalent to those seen with peripheral blood. These data correlate with secretion of IL-10 in the supernatant: upon re-activation, unpolarized cord blood T cells produced 5–10 fold higher levels of IL-10 (e.g., 40–130 ng/ml) in comparison to unpolarized peripheral blood T cells (e.g., 6–10 ng/ml). Thus, it was important to determine the relative roles of exogenous IL-10 and IFN-α in the differentiation of Tr1 cells from CD4+CD45RO− peripheral blood T cells. In contrast to cord blood T cells, it was necessary to add both exogenous IL-10 and IFN-α to CD4+CD45RO− peripheral blood T cells to differentiate cells with a Tr1-pattern of cytokine production. In comparison to cultures differentiated with IL-10 alone, cultures with IFN-α alone did not contain significantly more IL-10-producing cells. However addition of IFN-α alone did result in a decrease in the number of cells producing IL-2, IL-4, or IFN-γ. In contrast, addition of both IL-10 and IFN-α resulted in a significant increase in IL-10-producing cells. Detection of a population of cells with a Tr1-profile of cytokine production was directly correlated with an impaired ability of the culture to proliferate in response to polyclonal activation or alloantigens. Addition of IFN-α alone had little or no effect on the proliferative response, and only cells cultured in both IL-10 and IFN-α displayed the characteristic reduction in proliferation to polyclonal activation and a significant reduction in proliferation to alloantigens.

At the end of the primary and secondary stimulations, cord blood T cells were collected and counted in order to determine the increase in total cell number. Whereas cells cultured in IL-4, IL-12, or IL-10 and IFN-α similarly increased in cell number during the primary stimulation period, cells cultured in IL-10 and IFN-α did not significantly increase in number during the secondary stimulation period.

In order to better understand the mechanistic basis for the effects of IFN-α on T-cell proliferation and/or differentiation, it was tested whether IFN-α may have differential anti-proliferative effects on Tr1, Th1, and Th2 cells. It was possible that Tr1 cells were less susceptible to the anti-proliferative effects of IFN-α, and that the high number of IL-10-producing cells observed with IFN-α were not due to the differentiation of Tr1 cells, but rather to the fact that IFN-α prevented expansion of Th1 and Th2 cells. Cord blood T cells were activated in the presence of IL-4, IL-12, or IL-10, with or without IFN-α, for the primary stimulation. After 7 days, the cells were washed and re-stimulated in the presence of IL-4, IL-12, or IL-10, with or without IFN-α, and incorporation of $^3$H-thymidine was measured 3 days after initiation of the secondary stimulation. Addition of IFN-α, during the primary, secondary, or both the primary and secondary stimulation periods, had no significant effect on proliferation of cells cultured in IL-4, and only a modest effect on those cultured in IL-12 or IL-10. Together, these observations suggest that IFN-α acts, not as an antiproliferative agent, but rather as factor that drives the differentiation of Tr1 cells that, upon reactivation, suppress the proliferation of bystander non-Tr1 cells.

It has been shown that naive CD4+ T cells from cord blood or peripheral blood can be differentiated in vitro not only into Th1 or Th2 cells, but also into Tr1 cells. Similar to Th1 and Th2 cells, the differentiation of Tr1 cells is regulated by cytokines present upon T cell activation. There is strong evidence that the presence of IL-10 and IFN-α during T cell priming is necessary and sufficient to induce the differentiation of cells that produce IL-10, TGF-β, and IFN-γ, and display immunoregulatory properties. Furthermore, these observations suggest that Tr1 cells arise directly from a CD4+ T-cell precursor, and are not derived from the secondary differentiation of a Th1 or Th2 cell.

IL-10 alone, or in combination with TGF-$β_2$, was not sufficient to induce the differentiation of Tr1 cells. There is a difference between the cytokines required for the differentiation and the effector function of these cells. Type I interferons were potential candidates for cytokines involved in the differentiation of IL-10$^+$IFN-γ$^+$IL-4$^-$IL-2$^-$ cells. The receptors for IL-10 and IFN-α are structurally similar; both are members of the class II cytokine receptor family (Ho, et al. (1993) *Proc. Nat'l Acad. Sci. USA* 90:11267–11271) and they activate similar pathways of intracellular signal transduction. There are several reports showing that IFN-α stimulates the production of IL-10 and IFN-γ by CD4+ T cells. Demeure, et al. (1994) *J. Immunol.* 152:4775–4782; and McRae, et al. (1998) *J. Immunol.* 160:4298–4304. Moreover, it is well known that type I interferons inhibit the production of IL-4 (Demeure, et al. (1994) *J. Immunol.* 152:4775–4782; McRae, et al. (1997) *Eur. J. Immunol.* 27:2650–2656; and Schandene, et al. (1996) *J. Clin. Invest.* 97:309–315) and recently, it has been shown that IFN-α also inhibits the production of IL-2 (Erickson, et al. (1999) *Cell Growth Differ.* 10:575–582; and Zella, et al. (2000) *J. Immunol.* 164:2296–302). Indeed, addition of IFN-α, in combination with endogenous or exogenous IL-10, was sufficient to differentiate a population of IL-10$^+$IL-4$^-$IFN-γ$^+$IL-2$^-$ cells. Previous studies on the effects of IFN-α on CD4+ T cell differentiation have focussed on changes in IL-4 and IFN-γ production (Rogge, et al. (1998) *J. Immunol.* 16:6567–6574; and Rogge and Sinigaglia (1997) *Chem. Immunol.* 68:38–53) but, in the absence of analysis of IL-10 and IL-2 producing cells, it is impossible to evaluate the proportions of Th1 and Tr1 cells. It will be useful to determine if there is a role for IFN-α in combination with IL-10 in differentiation of Tr1 cells activated by APCs in vitro and/or in vivo.

Addition of IL-10 and IFN-α does not typically result in polarization towards a pure population of Tr1 cells. These cultures contain enough cells that possess a Tr1-profile of cytokine production to characterize the culture and exert regulatory effects. Tr1 cells displayed a low proliferative capacity following polyclonal activation and a profoundly suppressed ability to proliferate to alloantigens. These data correlate with our previous observations that Tr1 cells have an intrinsic low proliferative capacity (see Bacchetta, et al. (1994) *J. Exp. Med.* 179:493–502) and that they suppress proliferation of autologous naive T cells (Groux, et al. (1997) *Nature* 389:737–742). In addition, the inability to completely restore proliferation to alloantigens with neutralizing anti-IL-10 and anti-TGF-β antibodies mirrors the previous observations with Tr1 clones. Groux, et al. (1997) *Nature* 389:737–742. These data indicate that Tr1 cells express additional soluble or cell-surface proteins which are involved in regulation of immune responses.

Cord blood and peripheral blood CD4+ T cells differed in their requirements for exogenous cytokines for the differentiation of Tr1 cells. With cord blood T cells, addition of IFN-α alone was sufficient to induce a population of T cells with a Tr1-profile of cytokine production that displayed regulatory properties. It is likely that production of autocrine IL-10 by cord blood T cell alleviates the requirement for exogenous IL-10. In contrast, with peripheral blood T cells, which produce 5–10 fold less endogenous IL-10 compared to cord blood T cells, both exogenous IL-10 and IFN-α were required to induce the differentiation of Tr1 cells.

IL-10 and IFN-α can affect the growth of multiple cell types and previous studies have demonstrated that both cytokines can promote cell-cycle arrest in CD4+ T cells. Zella, et al. (2000) *J. Immunol.* 164:2296–302; Essayan, et al. (1999) *J. Allergy Clin. Immunol.* 103:451–457; Zagury, et al. (1998) *Proc. Nat'l Acad. Sci. USA* 95:3851–3856; and Perrin, et al. (1999) *Blood* 93:208–216. However, there are also reports documenting positive effects of both IL-10 (Groux, et al. (1998) *J. Immunol.* 160:3188–3193) and type I interferons (Marrack, et al. (1999) *J. Exp. Med.* 189:521–530; and Matikainen, et al. (1999) *Blood* 93:1980–1991), on survival and proliferation of T cells. There is the possibility that IFN-α may have differential effects on different T-cell subsets and the effects were tested of IFN-α on the proliferation of cells cultured in Th2-, Th1- or Tr1-polarizing conditions. In cultures where IFN-α was added during the primary and secondary stimulations, a striking decrease was observed in the total number of cells recovered at the end of the secondary stimulation. However, no significant anti-proliferative effects of IFN-α were observed, whether added during the primary, secondary, or both the primary and secondary stimulation periods, measured 3 days after activation in the secondary stimulation. These observations support the hypothesis that stimulation in the presence of IFN-α resulted in the differentiation of Tr1 cells which had a low proliferative capacity, and released suppressive cytokines which inhibited the growth of bystander, non-Tr1 cells in the culture.

The molecular mechanism(s) by which IL-10 and IFN-α induce the differentiation of Tr1 cells are unknown. It is well known that activation of the Jak/STAT pathway is the key intracellular pathway involved in differentiation of Th1 and Th2 cells. Murphy, et al. (2000) *Ann. Rev. Immunol.* 18:495–527. In fact, recently it has been shown that activation of STAT-6 is sufficient to induce differentiation of Th2 cells. Kurata, et al. (1999) *Immunity* 11:677–688. IL-10 activates STAT-1 and STAT-3 (Finbloom and Winestock (1995) *J. Immunol.* 155:1079–1090; and Ho, et al. (1995) *Mol. Cell. Biol.* 15:5043–5053), whereas IFN-α activates STAT-1, -2, and -3 in most cells (Leonard and O'Shea (1998) *Ann. Rev. Immunol.* 16:293–322), and in human lymphocytes can also activate STAT-4 and -5 (Rogge, et al. (1998) *J. Immunol.* 16:6567–6574; and Matikainen, et al. (1999) *Blood* 93:1980–1991). It will be useful to define activation of which particular members of the Jak/STAT pathway are also required for the differentiation of Tr1 cells.

Recently, it has been shown that, in the human, the principal type-1 interferon producing cells are type 2 dendritic cells (DC2; Cella, et al. (1999) *Nature Med.* 5:919–923; and Siegal, et al. (1999) *Science* 284:1835–1837). Although it is unclear whether priming by DC2 cells results in polarization of naive T cells towards Th1 or Th2 subsets, it is interesting to speculate that, via production of IFN-α, DC2 cells may also be involved in the differentiation of Tr1 cells. Thus, in addition to its anti-viral effects, IFN-α may also be involved in regulation of immune responses.

That Tr1 cells can be differentiated in vitro from CD4+ cord blood T cells following polyclonal activation in the presence of IFN-α has been shown. Differentiation of Tr1 cells from CD4+ peripheral blood T cells required addition of both IL-10 and IFN-α. In addition to their unique profile of cytokine production, in vitro-differentiated Tr1 cells possessed regulatory functions that were partially dependent on IL-10 and TGF-β. The ability to isolate and culture these cells in vitro is a crucial step towards learning more about the basic biology of these cells and exploring the possibility that Tr1 cells can be used as a "cellular therapy" to regulate immune responses to self- or allo-antigens in vivo.

Tr1 cells are characterized, in part, by their unique cytokine profile: they produce high levels of IL-10, significant levels of TGF-β and IFN-γ, but little or no IL-4 or IL-2. The cytokine production is typically evaluated in cultures of $10^6$ cells/ml/48 h. High levels of IL-10 correspond to at least about 6000 pg/ml, typically greater than about 8, 10, 12, 14, 16, 18, or 20 thousand pg/ml or more. Significant levels of TGF-β correspond to at least about 100 pg/ml, typically greater than about 200, 300, 400, 600, 800, or 1000 pg/ml or more. Significant levels of IFN-γ correspond to at least about 400 pg/ml, typically greater than about 600, 800, 1000, 1200, 1400, 1600, 1800, or 2000 pg/ml or more. Little or no IL-4 or IL-2 correspond to less than about 200 pg/ml, preferably less than about 150, 100, 75, or 50 pg/ml, or less.

A number of experiments were designed to determine the effects of IL-10, IFN-α, and IL-15 on the differentiation of IL-10-producing T cells. Efforts have focussed on aspects of the differentiation system described by Sornasse, et al., supra, which involves co-culture of CD4+ T cells with irradiated L-cells, expressing CD32, CD58, and CD80, in the presence of anti-CD3, IL-2, and/or IL-15, and polarizing cytokines. Following two rounds of stimulation, cells are collected, stimulated with αCD3 and αCD28, and analyzed by intra-cytoplasmic staining and ELISA for the production of IL-10, IL-4, IL-2, and IFN-γ. Experiments were initiated with CD4+ T cells derived from cord blood, which cells have an innate ability to produce high levels of IL-10. Addition of IFN-α resulted in a significant, e.g., 5–6 fold, increase in the percentage of IL-10-positive cells compared to addition of IL-10 alone. Consistent with a Tr1 phenotype, approximately 50% of the IL-10 positive cells were also positive for IFN-γ. Further efforts are underway to determine the percentage of IL-10+IL-4- and IL-10+IL-2-cells at the single cell level. In order to definitively establish the percentage of Tr1 cells differentiated in vitro, we plan to perform limiting dilutions (after the secondary stimulation) in the presence of allogeneic feeder-cell mixture and to analyze the profile of cytokine production at the clonal level.

It was observed that in cord blood T cells the differentiation of IL-10-producing cells could be induced by IFN-α alone, and did not require addition of exogenous IL-10. This may be because cord blood T cells have an innate ability to make endogenous IL-10 and thus the addition of exogenous IL-10 may be dispensable for differentiation of Tr1 cells.

The mechanism by which IFN-α promotes the differentiation of IL-10-positive cells is presently unclear. It is likely that this cytokine has a direct effect on naive T cells since the receptors for IL-10 and type I Interferons are structurally similar (they are in the same subfamily) and have very similar intracellular signal transduction pathways. However, since IFN-α acts cross-species, it is possible that it has indirect effects on the murine L-cells in this culture system. Thus, it will be useful to determine the effects of IFN-α on the generation of IL-10-positive T cells stimulated with immobilized anti-CD3 and anti-CD28.

Based on the observations that IL-15 can promote the growth of Tr1 clones, the effects of IL-15 on the differentiation of IL-10-producing cells were investigated. It is clear that in the presence of exogenous IL-10 and IFN-α, addition of both IL-2 and IL-15 results in the highest percentage of IL-10-postive cells. Additional experiments are underway to determine whether IL-15 is acting as a differentiation and/or a growth factor. The observation that addition of IL-15 to cultures of Th2 cells (IL-4 plus αIL-12) or Th1 cells (IL-12 plus αIL-4) also results in an increase of IL-10-positive cells suggests that IL-15 may directly influence the production of IL-10 (e.g., acting as a differentiation factor). No increase was observed in the proliferation of cells in the presence of IL-15 compared to IL-2 alone.

Importantly, cord blood T cells stimulated in the presence of IFN-α have markedly different growth rates in the primary and secondary stimulations. Addition of IFN-α in the primary stimulation does not have a significant antiproliferative effect, and the cultures expand similarly to control Th1 and Th2 cultures. However, in the secondary stimulation, the cultures with IFN-α expand significantly less than control cultures. This decreased proliferation during the secondary stimulation may be the result of the fact that Tr1 cells have been differentiated and they suppress the proliferation of bystander non-Tr1 cells. Alternatively, IFN-α could have differential effects on the proliferation of naive and memory T cells.

In contrast to cord blood T cells, initial results suggest that addition of IFN-α, IL-10, and IL-15 is required for the optimal differentiation of IL-10-positive T cells from peripheral blood. This observation suggests that exogenous IL-10 is required for differentiation of Tr1 cells unless high levels of endogenous IL-10 are present, as in cord blood. Furthermore, these data confirm that IL-15 has a critical role in the differentiation and/or growth of cells producing high levels of IL-10. Experiments are underway to determine the optimal conditions to differentiate Tr1 cells from peripheral blood.

III. Uses

The present invention also provides efficient methods for preparing and using antigen-specific anergic T cells, which fail to respond in an antigen-specific fashion to representation of the antigen. See, e.g., Paul (ed. 1997) *Fundamental Immunology* Raven Press. This antigen-specific anergy can be distinguished from generic tolerance in that many forms of tolerance result from blockage of the T cell receptor signal at the cell surface and thus will be independent of the antigen. The antigen-specific anergy does not appear to affect the $Ca^{++}$ dependent signaling pathway, e.g., the Ras/Raf/MAPK pathway, of signal transduction, since the T cell receptor and the $Ca^{++}$ flux responses to antigen engagement remain. Moreover, the anergy does not require constant administration of an agent to block the early stages of signal transduction, e.g., necessary to actively block T cell receptor function. The anergy seems to be maintained for a period of time, e.g., for at least about 14 days, 18 days, 21 days, 24 days, etc. It may remain for weeks, months, and preferably years.

Antigen-specific anergy can be produced by presenting a combination of IL-10 with antigen, and the present invention provides means to improve the cell yields. The components are presented to the immune system, or cells thereof, for adequate periods of time, often completely coextensive, though the period may not necessarily require both components for the entire duration. This period will typically be at least about 5 days, more typically at least about 7 days, preferably at least about 9–11 days, and more preferably at least about 13–15 days or more. The dosing of the IL-10, IFN-α, and or antigen may depend on various factors, including, e.g., the antigen, the duration of the periods, whether both are present, whether the IL-10 is presented before antigen, etc. Preferably, the components are presented for at least about 7 days. The use of IFN-α and IL-15 in the cultures vastly improve efficiency.

IL-10 has been described before. See, e.g., deVries and de Waal Malefyt (eds. 1995) Interleukin-10 Landes, Austin, Tex. Other means to effect higher IL-10 levels include stimulation of endogenous IL-10, including, e.g., LPS, TNF-α, IL-12, BCG1 (Bacillus Calmett Guerin), Corynebacterium parvus, poly I-C (alloadjuvant for activating monocytes and macrophages), etc. Other methods are known to induce IFN-α and IL-15, e.g., with LPS, virus infection, poly-I-C, or CD40. See, e.g., Siegel, et al. (1999) Science 284:1835–1837; de Maeyer and de Maeyer-Guignard "Interferons" in Thomson (ed. 1998) The Cytokine Handbook, Academic Press, London; Meager "Interferons Alpha, Beta and Omega" in Marie-Sluis and Thorpe (eds. 1998) Cytokines, Academic Press, NY; Kennedy, et al. "Interleukin-15" in Thomson (ed. 1998) The Cytokine Handbook, Academic Press, London; and Ballaun "Interleukin-15" in Marie-Sluis and Thorpe (eds. 1998) Cytokines, Academic Press, NY. Virus infection induces monocytes and the natural Interferon Producing Cells (IPC). Agonistic antibodies to the IL-10 receptor may also function as an agonist.

Various types of antigens exist for which antigen-specific T cell anergy may be important. Both alloantigens and self antigens are presented in the context of MHC. See, e.g., Paul (ed.) Fundamental Immunology. Other antigens for which T cell anergy may be important include soluble antigens, e.g., soluble proteins or fragments of insoluble complexes, particulate antigens, e.g., bacteria or parasites, and allergens. Various forms of antigen will be presented with IL-10 to induce antigen-specific anergy. Culturing in IFN-α will increase Tr1 yields, and culturing in IL-15 maintains some Tr1 features.

Antigen-specific anergy involves a mechanism which is distinguishable from certain other forms of non-responsiveness. These Tr1 cells appear to be memory T cells, e.g., CD45+, in contrast to naive T cells, e.g., CD45RA+ or CD45RO−. In particular, this antigen-specific anergy reflects the inability of these antigen-specific cells to respond to subsequent restimulation with the specific antigen, typically with IL-2. When antigen-specific anergic cells are restimulated with IL-2 and antigen at normal levels, the cells fail either to proliferate significantly, or to produce the cytokines. However, the anergic population containing Tr1 cells, when stimulated in a subsequent presentation with anti-CD3 antibodies (at about 100 ng/ml) will stimulate only the growth of the Th0, Th1, and Th2 T cells. Analysis of the cytokine production by these defined T helper subset cells is well known when stimulated at the higher levels of anti-CD3 of about 1–10 μg/ml. However, at this level of stimulation, the Tr1 cells seem not to be stimulated to proliferate or produce cytokines. The Tr1 cells seem to be stimulated both to proliferate and produce cytokines with anti-CD3 antibodies at about 100–700 μg/ml. Thus, if the cells in a mixed population are diluted out to single cells in wells, all of the T helper subsets will be stimulated with anti-CD3 antibodies at the 100–700 μg/ml, which allows evaluation of the cytokine production profiles of the different subsets Th0, Th1, Th2, and Tr1.

The response to subsequent anti-CD3 antibody general stimulation, e.g., through the T cell receptor/Cd3 complex, can be quantitated by various methods. Various cytokines may be measured according to biological activity. Preferably, a quantitation of accumulated protein may be determined by various immuno-, activity, or other assays. Alternatively, mRNA production may be measured to establish levels of stimulation of transcription.

Typically, cytokines are measured after accumulation of secreted protein over set periods of time upon subsequent, e.g., secondary or subsequent, stimulation using anti-CD3 antibody (100–700 μg/ml) or cognate antigen. Thus, the time for accumulation is preferably at least about 24 h in a volume of about 1 ml, but may be longer, and may include other feeder cell layers, etc.

Cell proliferation after subsequent stimulation can be measured by standard methods. Often this includes measuring incorporation of nucleotides, but may also involve measuring cell numbers, cell volumes, etc.

While certain responses of tolerance characterized as anergy result from blockage of signaling at the T cell receptor (see Weiss and Liftman (1994) Cell 76:263–274; Chan, et al. (1994) Ann. Rev. Immunol. 12:555–592; and Fraser, et al. (1993) Immunol. Today 14:357–362), the anergy described herein exists with functional T cell receptor. In particular, stimulation with anti-CD3 still results in a $Ca^{++}$ flux. But the antigen-specific T cells do not respond to the antigen stimulation in the normal manner, e.g., by production of cytokines and/or cell proliferation.

The anergy provided herein involves either a much lowered proliferative responsiveness to IL-2 and/or antigen, e.g., less than about 50% response, usually less than about 40% response, more usually less than about 30% response, preferably less than about 20%, and more preferably 10%, or less as compared to non-anergic cells. Alternatively, the stimulation required to induce a response requires much larger amounts of IL-2 and antigen, e.g., 5–50x, to elicit the equivalent proliferative response. The anergy also is reflected in a different cytokine production profile upon restimulation of clones with anti-CD3 antibodies.

The measure of cytokine production is after restimulation of clones with the specific antigen, although more usually after generic stimulation with anti-CD3 (in vitro at about 10 μg/ml or more), which apparently activates through the T cell receptor. This stimulation results in a much attenuated cellular proliferation response, and a distinguishable cytokine production profile. Among the notable differences in cytokine production after restimulation and cloning are undetected IL-4 and high IL-10 production. The amount of anti-CD3 antibodies used can also affect the response.

The duration of IL-10 with antigen can affect the extent of reversibility. While treatments over about 7 days leads to substantial irreversibility with normal amounts of IL-2 or anti-CD3 antibody (10 μg/ml); very high amounts of IL-2, antigen, or anti-CD3 antibody (e.g., 700 μg/ml) will tend to have a greater capacity to either attenuate or reverse the anergy. Similarly, the contacting with IFN-α and/or IL-15 may affect reversibility.

IL-10 inhibited, in a dose-dependent fashion, the alloantigen-induced proliferative responses in primary mixed lymphocyte response. The suppressive effect was optimal when IL-10 was added at the beginning of the cultures suggesting that it acts on the early stages of T cell activation. The proliferative responses were enhanced in the presence of anti-IL-10 mAb, indicating that endogenously produced IL-10 suppresses proliferation in primary MLR. The inhibitory effects of IL-10 were observed irrespective of whether irradiated allogeneic peripheral blood mononuclear cells (PBMC), purified monocytes, or B cells were used as stimulator cells. The reduced proliferative responses were not restored by high concentrations of exogenous IL-2 indicating that the effects of IL-10 are not related to inhibition of IL-2 synthesis. Furthermore, the production of IL-2, IFN-γ, IL-6, GM-CSF, and TNF-α in primary MLR was diminished by IL-10 and enhanced in the presence of anti-IL-10 mAb. The strongest effects were observed on the production of IFN-γ. Although IL-10 reduces the proliferative responses, the ratio of CD3$^+$CD4$^+$ and CD3$^+$CD8$^+$ T cells remained the same in IL-10 treated and control cultures. However, the percentages of activated CD3$^+$ T cells as judged by CD25$^+$ and HLA-DR$^+$ expression were consistently reduced in the presence of IL-10.

h-IL-10 inhibits the synthesis of IFN-γ and granulocyte-macrophage colony stimulating factor (GM-CSF) induced in human PBMC by PHA, anti-CD3 mAb, and IL-2 (Bacchetta, et al. (1989) *J. Immunol.* 144:902; and Bevan (1984) *Immunol Today* 5:128. This inhibition occurs at the transcriptional levels (Altmann, et al. (1989) *Nature* 338:512; Bacchetta, et al., supra). Murine IL-10 (m-IL-10) has pleiotropic activities on different cell types, including growth promoting effects on thymocytes (Chen, et al. (1991) *J. Immunol.* 147:528), cytotoxic T cells (De Koster, et al. (1989) *J. Exp. Med.* 169:1191), and mast cells (de Waal Malefyt, et al. (1991) *J. Exp. Med.* 174:1209). m-IL-10 induces class II MHC antigen expression on B cells and sustains the viability of these cells (de Waal Malefyt, et al. (1991) *J. Exp. Med.* 174:915). Furthermore, IL-10 inhibits cytokine production by macrophages (Bejarano, et al. (1985) *Int. J. Cancer* 35:327; Fiorentino, et al. (1989) *J. Exp. Med.* 170:2081). h- and m-IL-10 have extensive homology to BCRF-1, an open reading frame of the Epstein Barr virus (EBV) genome (Azuma, et al. (1992) *J. Exp. Med.* 175:353; Bacchetta, et al. (1989) *J. Immunol.* 144:902). The protein product of BCRF-1, designated viral IL-10 (v-IL-10), shares most properties with h-and m-IL-10 including CSIF activity on human and mouse T cells (Bacchetta, et al., supra; Bevan, M. J., supra).

h-IL-10 and v-IL-10 inhibit antigen specific proliferative responses by reducing the antigen presenting capacity of human monocytes via downregulation of class II MHC molecules (Figdor, et al. (1984) *J. Immunol. Methods* 68:68). Moreover, IL-10 inhibits cytokine synthesis by LPS or IFN-γ activated monocytes, including CM-CSF, G-CSF, and the proinflammatory cytokines IL-1α, IL-1β, IL-6, IL-8, and TNF-α (Bejarano, et al. (1985) *Int. J. Cancer* 35:327; Fiorentino, et al, supra.). Interestingly, LPS activated monocytes produce high levels of IL-10, and enhanced production of cytokines was observed in the presence of anti-IL-10 mAb indicating an autoregulatory effect of IL-10 on monokine production (Bejarano, et al., supra).

Alloreactivity reflects, at least in part, recognition of foreign MHC molecules plus antigenic peptides of various origin (Fiorentino, et al. (1991) *J. Immunol.* 146:3444; Fiorentino, et al. (1991)*J. Immunol.* 147:3815; Freedman, et al. (1987) *J. Immunol.* 139:3260; Go, et al. (1990) *J. Exp. Med.* 172:1625). Moreover, alloreactive T cells may recognize conformational differences between MHC molecules largely independent of the peptides bound, or even on empty MHC molecules (Harding, et al. (1990) *Proc. Natl. Acad. Sci. USA* 87:5553; Hsu, et al. (1990) *Science* 250:830; Julius, et al. (1973) *Eur. J. Immunol.* 3:645). IL-10 inhibits allospecific proliferative responses, and cytokine production In addition, the reduced proliferative responses could not be restored by exogenous IL-2.

Thus, the present invention provides means to generate large quantities of alloantigen specific Tr1 cells by stimulating host derived CD4+ T cells with donor derived irradiated PBMC in the presence of IL-10, e.g., for minimally at least about 3 days, preferably at least about 5 days, more preferably at least about 7 days, and in certain embodiments 9, 11, 13, 15, or more days. Methods are provided to increase yields of Tr1 cells, allowing for more effective therapeutic application. The cells can be administered prior or simultaneously with the transplant (organ or bone marrow). The transplant event and/or therapy may be with or without administration of IL-10, IFN-α, and/or IL-15.

The above cell therapy can be extended to treat other chronic diseases causing by antigens, such as gliadin (e.g., gluten) for the treatment of coeliac disease, allergens for the treatment of chronic allergic diseases (asthma, atopic dermatitis, rhinitis), or GAD (glutamic acid decarboxylase) or insulin for the treatment of diabetes.

In addition, this may provide treatment for inappropriate sensitivity to many other potential autoantigens. The cells or treatment may provide means for induction of long term tolerance and Tr1 cell development in vivo. Long term, e.g., 5–15 day treatment with IL-10 may enhance in vivo production of anergy, with copresentation of appropriate MHC antigens, e.g., with class I or class II, or other soluble antigens. The IFN-α and IL-15 methods may greatly improve numbers of cells, and effectiveness of treatment.

The invention also provides means for administration of IL-10, with or without IFN-α and/or IL-15, in order to induce antigen specific Tr1 cells and long term antigen specific tolerance in vivo for the treatment of diseases with undesired T-cell activation, e.g., in transplant rejection, graft versus host disease, parasitic diseases, chronic inflammatory diseases such as Crohn's disease, colitis, chronic inflammatory eye diseases, chronic inflammatory lung diseases, and chronic inflammatory liver diseases. See, e.g., Frank, et al. (eds.) *Samter's Immunologic Diseases* Little, Brown, Boston, Mass.

In other contexts, it may be useful to administer of IL-10 in order to induce autoantigen specific Tr1 cells and autoantigen specific tolerance in vivo for the treatment of autoimmune diseases such as rheumatoid arthritis, diabetes, multiple sclerosis.

In many embodiments, the IL-10 should be typically administered for a minimum of 5–15 days, preferably at least about 7 days.

When administered parenterally the therapeutics will be formulated in a unit dosage injectable form (solution, suspension, emulsion) in association with a pharmaceutically acceptable parenteral vehicle. Such vehicles are inherently nontoxic and nontherapeutic. The cytokines may be administered in aqueous vehicles such as water, saline, or buffered vehicles with or without various additives and/or diluting agents. Alternatively, a suspension, such as a zinc suspension, can be prepared to include the peptide. Such a suspension can be useful for subcutaneous (SQ), intradermal (ID), or intramuscular (IM) injection. The proportion of therapeutic entity and additive can be varied over a broad range so long as both are present in effective amounts. The therapeutic is preferably formulated in purified form substantially free of aggregates, other proteins, endotoxins, and the like, at concentrations of about 5 to 30 mg/ml, preferably 10 to 20 mg/ml. Preferably, the endotoxin levels are less than 2.5 EU/ml. See, e.g., Avis, et al. (eds. 1993) *Pharmaceutical Dosage Forms: Parenteral Medications* 2d ed., Dekker, NY; Lieberman, et al. (eds. 1990) *Pharmaceutical Dosage Forms: Tablets* 2d ed., Dekker, NY; Lieberman, et al. (eds. 1990) *Pharmaceutical Dosage Forms: Disperse Systems* Dekker, NY; Fodor, et al. (1991) *Science* 251:767–773;

Coligan (ed.) *Current Protocols in Immunology*; Hood, et al. *Immunology* Benjamin/Cummings; Paul (ed. 1997) *Fundamental Immunology* 4th ed., Academic Press; Parce, et al. (1989) *Science* 246:243–247; Owicki, et al. (1990) *Proc. Nat'l Acad. Sci. USA* 87:4007–4011; and Blundell and Johnson (1976) *Protein Crystallography*, Academic Press, New York.

Selecting an administration regimen for a therapeutic agonist or antagonist depends on several factors, including the serum or tissue turnover rate of the therapeutic, the immunogenicity of the therapeutic, or the accessibility of the target cells. Preferably, an administration regimen maximizes the amount of therapeutic delivered to the patient consistent with an acceptable level of side effects. Accordingly, the amount of therapeutic delivered depends in part on the particular agonist or antagonist and the severity of the condition being treated. Guidance in selecting appropriate doses of antibodies is found in the literature on therapeutic uses, e.g. Bach et al., chapter 22, in Ferrone, et al. (eds. 1985) *Handbook of Monoclonal Antibodies* Noges Publications, Park Ridge, N.J.; and Russell, pgs. 303–357, and Smith et al., pgs. 365–389, in Haber, et al. (eds. 1977) *Antibodies in Human Diagnosis and Therapy* Raven Press, New York, N.Y.

Determination of the appropriate dose, e.g., of Tr1 cells, is made by the clinician, e.g., using parameters or factors known in the art to affect treatment or predicted to affect treatment. Generally, the dose begins with an amount somewhat less than the optimum dose and it is increased by small increments thereafter until the desired or optimum effect is achieved relative to any negative side effects. Preferably, a therapeutic that will be used is derived from the same species as the animal targeted for treatment, thereby minimizing a humoral response to the reagent.

The total weekly dose ranges for antibodies or fragments thereof range generally from about 1 ng, more generally from about 10 ng, typically from about 100 ng; more typically from about 1 $\mu$g, more typically from about 10 $\mu$g, preferably from about 100 $\mu$g, and more preferably from about 1 mg per kilogram body weight. Although higher amounts may be more efficacious, the lower doses typically will have fewer adverse effects. Generally the range will be less than 100 mg, preferably less than about 50 mg, and more preferably less than about 25 mg per kilogram body weight.

The weekly dose ranges for antagonists, e.g., antibody, binding fragments, range from about 10 $\mu$g, preferably at least about 50 $\mu$g, and more preferably at least about 100 $\mu$g per kilogram of body weight. Generally, the range will be less than about 1000 $\mu$g, preferably less than about 500 $\mu$g, and more preferably less than about 100 $\mu$g per kilogram of body weight. Dosages are on a schedule which effects the desired treatment and can be periodic over shorter or longer term. In general, ranges will be from at least about 10 $\mu$g to about 50 mg, preferably about 100 $\mu$g to about 10 mg per kilogram body weight.

Agonists of the ligands, e.g., cytokines, are also contemplated. Hourly dose ranges for muteins range from at least about 10 $\mu$g, generally at least about 50 $\mu$g, typically at least about 100 $\mu$g, and preferably at least 500 $\mu$g per hour. Generally the dosage will be less than about 100 mg, typically less than about 30 mg, preferably less than about 10 mg, and more preferably less than about 6 mg per hour. General ranges will be from at least about 1 $\mu$g to about 1000 $\mu$g, preferably about 10 $\mu$g to about 500 $\mu$g per hour.

In particular contexts, e.g., transplant, may involve the administration of the therapeutics in different forms. For example, in an organ transplant or skin graft, the tissue may be immersed in a sterile medium containing the therapeutic resulting in a prophylactic effect on cell migration soon after the transplant is applied.

The phrase "effective amount" means an amount sufficient to effect a desired response, or to ameliorate a symptom or sign of the medical condition. Typical mammalian hosts will include mice, rats, cats, dogs, and primates, including humans. An effective amount for a particular patient may vary depending on factors such as the condition being treated, the overall health of the patient, the method, route, and dose of administration and the severity of side affects. Preferably, the effect will result in a change in quantitation of at least about 10%, preferably at least about 20%, 30%, 50%, 70%, or even 90% or more. When in combination, an effective amount is in ratio to a combination of components and the effect is not limited to individual components alone.

An effective amount of therapeutic will modulate the symptoms typically by at least about 10%; usually by at least about 20%; preferably at least about 30%; or more preferably at least about 50%. Such will result in, e.g., statistically significant and quantifiable changes. This may be an increase or decrease in the numbers of target cells being attracted within a time period or target area.

The present invention provides reagents and methods which will find use in therapeutic applications as described. See, e.g., Berkow (ed.) *The Merck Manual of Diagnosis and Therapy*, Merck & Co., Rahway, N.J.; Thorn, et al. *Harrison's Principles of Internal Medicine*. McGraw-Hill, NY; Gilman, et al. (eds. 1990) *Goodman and Gilman's: The Pharmacological Bases of Therapeutics*, 8th Ed., Pergamon Press; *Remington's Pharmaceutical Sciences*, 17th ed. (1990), Mack Publishing Co., Easton, Pa.; Langer (1990) *Science* 249:1527–1533; and *Merck Index*, Merck & Co., Rahway, N.J.

Antibodies to markers may be used for the identification or sorting of Tr1 cell populations. Methods to sort such populations are well known in the art, see, e.g., Melamed, et al. (1990) *Flow Cytometry and Sorting* Wiley-Liss, Inc., New York, N.Y.; Shapiro (1988) *Practical Flow Cytometry* Liss, New York, N.Y.; and Robinson, et al. (1993) *Handbook of Flow Cytometry Methods* Wiley-Liss, New York, N.Y. Populations of cells can also be purified, e.g., using magnetic beads as described, e.g., in Bieva, et al. (1989) *Exp. Hematol.* 17:914–920; Hernebtub, et al. (1990) *Bioconj. Chem.* 1:411–418; Vaccaro (1990) *Am. Biotechnol. Lab.* 3:30.

The broad scope of this invention is best understood with reference to the following examples, which are not intended to limit the inventions to the specific embodiments.

EXAMPLES

I. General Methods

Some of the standard methods are described or referenced, e.g., in Maniatis, et al. (1982) *Molecular Cloning, A Laboratory Manual*, Cold Spring Harbor Laboratory, Cold Spring Harbor Press; Sambrook, et al. (1989) *Molecular Cloning: A Laboratory Manual*, (2d ed.), vols. 1–3, CSH Press, NY; Ausubel, et al., *Biology*, Greene Publishing Associates, Brooklyn, N.Y.; or Ausubel, et al. (1987 and Supplements) *Current Protocols in Molecular Biology*, Greene/Wiley, New York; Innis, et al. (eds.) (1990) *PCR Protocols: A Guide to Methods and Applications* Academic Press, N.Y. Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification" in *Methods in Enzymology*, vol. 182, and other volumes in this series; manufacturer's literature on use of protein purification products, e.g., Pharmacia, Piscataway, N.J., or Bio-Rad, Richmond, Calif.; and Coligan, et al. (eds.) (1995 and periodic supplements) *Current Protocols in Protein Science*, John Wiley & Sons, New York, N.Y. Combination with recombinant techniques allow fusion to appropriate segments, e.g., to a FLAG sequence or an equivalent which can be fused via a protease-removable sequence. See, e.g., Hochuli (1989) *Chemische Industrie* 12:69–70; Hochuli (1990) "Purification of Recombinant Proteins with Metal Chelate Absorbent" in Setlow (ed.) *Genetic Engineering Principle and Methods* 12:87–98, Plenum Press, N.Y.; and Crowe, et al. (1992) *QIAexpress: The High Level Expression & Protein Purification System* QIAGEN, Inc., Chatsworth, Calif.

Standard immunological techniques are described, e.g., in Hertzenberg, et al. (eds. 1996) *Weir's Handbook of Experimental Immunology* vols. 1–4, Blackwell Science; Coligan (1991) *Current Protocols in Immunology* Wiley/Greene, NY; and *Methods in Enzymology* volumes. 70, 73, 74, 84, 92, 93, 108, 116, 121, 132, 150, 162, and 163.

FACS analyses are described in Melamed, et al. (1990) *Flow Cytometry and Sorting* Wiley-Liss, Inc., New York, N.Y.; Shapiro (1988) *Practical Flow Cytometry* Liss, New York, N.Y.; and Robinson, et al. (1993) *Handbook of Flow Cytometry Methods* Wiley-Liss, New York, N.Y.

II. Cell Purification

All human tissue was obtained from healthy anonymous donors in accordance with local ethical committee approval. Human neonatal leukocytes from umbilical cord blood were prepared by centrifugation over a Ficoll-Hypaque gradients (Nycomed Amersham, Uppsala, Sweden), and CD4+ T cells were purified by positive or negative selection. For negative selection, purification was performed by addition of Dynabeads (Dynal, Oxoid, Italy) coupled to antibodies against CD8, CD14, CD19 and CD56. Beads were added at a 4:1 bead/target cell ratio and incubated for 1 h at 4° C. Beads and contaminating cells were removed by magnetic field. For positive selection, cells were purified using the Miltenyi CD4+ T cell isolation kit according to the manufacturer's instructions (Miltenyi Biotech, Gladbach, Germany). Results obtained with CD4+ T cells isolated by negative or positive selection were identical. Human peripheral blood mononuclear cells (PBMCs) were centrifuged over Ficoll-Hypaque gradients, adherent cells were removed by 2 rounds of incubation on tissue-culture treated flasks for one hour at 37° C., and CD4+CD45RO− cells were purified by negative selection. Non-adherent cells were incubated with anti-CD45RO antibodies (5 $\mu$g/$10^6$ target cells; UCHL1, Valter Occhiena, Torino, Italy) for 45 min at 4° C. Following washing, Dynabeads coupled to antibodies directed against CD8, CD14, CD19, CD56, and mouse IgG were added, and CD4+CD45RO− cells were isolated as described above.

III. T Cell Differentiation

Murine L-cell transfectants expressing CD32 (FCγRII), human CD58 (LFA-3), and human CD80 (de Waal Malefyt, et al. (1993) *Eur. J. Immunol.* 23:418–424), were cultured in RPMI 1640 (BioWhittaker, Bergamo, Italy) supplemented with 10% FCS (Mascia Brunelli, Italy), 100 U/ml penicillin/ streptomycin (Bristol-Myers Squibb, Italy), and 2 mM glutamine (Gibco-BRL, Milan, Italy). L-cells were detached by incubation with trypsin-EDTA (Gibco-BRL), irradiated (7000 Rad) by an X-ray source. Following washing, cells were plated in 24 well plates (Corning, Cambridge, Mass.) at an initial density of $4 \times 10^5$ cells/ml in a 500 $\mu$l volume of Yssel medium (Diaclone, France) supplemented with 10% FCS, 1% pooled human AB serum, and 100 U/ml penicillin/ streptomycin (hereafter referred to as complete medium) and 100 ng/ml of anti-CD3 (OKT3, Orthoclone, Jansen Cilag, Italy). After the L-cells had adhered, 500 $\mu$l of CD4+ cord blood or CD4+CD45RO− peripheral blood T cells were added at an initial density of $4 \times 10^5$ cells/ml in complete medium. For differentiation by immobilized anti-CD3, the antibody (10 $\mu$g/ml) was immobilized by overnight incubation in 24 well plates in 0.1 M Tris, pH 9.5. Wells were washed 3 times with PBS before addition of $10^6$ CD4+ cord blood T cells in complete medium.

Other work in this laboratory has shown that Tr1 clones proliferate better in the presence of IL-15 than IL-2, whereas Th1 and Th2 clones proliferate equally well in response to either cytokine. Therefore, all experiments were performed in the presence of rhIL-2 (100 U/ml; Chiron Italia, Italy) and rhIL-15 (5 ng/ml; Peprotech, Rocky Hill, N.J.). In addition, the following polarizing cytokines were added as indicated: rhIL-10 (100 U/ml; Schering-Plough Research Institute, Kenilworth, N.J.), rhIFN-α (5 ng/ml; Schering-Plough Research Institute), rhIL-4 (200 U/ml; Schering-Plough Research Institute), rhIL-12 (5 ng/ml; R&D Systems, Minneapolis, Minn.), TGFβ$_2$ (1 ng/ml; R&D Systems, MN). Anti-human IL-4 antibodies (200 ng/ml; Pharmingen, San Diego, Calif.) and anti-human IL-12 antibodies (10 $\mu$g/ml; Pharmingen) were added to the Th1 and Th2 polarizing conditions, respectively. T cells were split as necessary, IL-2 and IL-15 were replenished in all groups, and IL-4 was replenished only in cultures of Th2 cells. At day 7, T cells were collected, washed, counted, and restimulated under identical conditions for an additional 7 days. At day 14 of in vitro culture, cells were collected, washed, counted and analyzed for their profile of cytokine production and proliferative capacity. All cells were cultured in humidified incubators at 37° C., with 5% $CO_2$.

CD4+ cord blood T cells were activated by anti-CD3 antibodies crosslinked on CD32+CD80+CD58+ L-cells in the presence of IL-10 and/or TGFβ$_2$. Following two rounds of identical stimulation, T cells were restimulated with immobilized anti-CD3 (10 $\mu$g/ml) and soluble anti-CD28 (1 $\mu$g/ml) antibodies and cytokine production was determined by intracytoplasmic staining and cytofluorometric analysis.

CD4+ cord blood T cells were activated by anti-CD3 antibodies cross-linked on CD32+CD80+CD58+ L-cells or immobilized on plastic, in the presence of IL-4, IL-12, or IL-10 and IFN-α. Following two rounds of identical stimulation, T cells were re-stimulated with immobilized anti-CD3 (10 $\mu$g/ml) and soluble anti-CD28 (1 $\mu$g/ml) antibodies and cytokine production was determined by intracytoplasmic staining and cytofluorometric analysis.

CD4+ cord blood were activated by anti-CD3 antibodies cross-linked on CD32+CD80+CD58+ L-cells in the presence of IL-10 and/or IFN-α. Following two rounds of identical stimulation, T cells were re-stimulated with immobilized anti-CD3 (10 $\mu$g/ml) and soluble anti-CD28 (1 $\mu$g/ml) antibodies and cytokine production was determined by intracytoplasmic staining and cytofluorometric analysis. In parallel, T cells were tested for their ability to proliferate in response to polyclonal activation by immobilized anti-CD3 (10 $\mu$g/ml) and soluble anti-CD28 (1 $\mu$g/ml) antibodies or CD3-depleted allogeneic PBMCs (MLR). Proliferation was measured by incorporation of $^3$H-thymidine into de novo synthesized DNA 3 days after initiation of the culture.

CD4+CD45RO− peripheral blood T cells were activated by anti-CD3 antibodies cross-linked on CD32+CD80+CD58+ L-cells in the presence of IL-10 and/or IFN-α. Following two rounds of identical stimulation, T cells were re-stimulated with immobilized anti-CD3 (10 $\mu$g/ml) and soluble anti-CD28 (1 $\mu$g/ml) antibodies and cytokine production was determined by intracytoplasmic staining and cytofluorometric analysis. In parallel, T cells were tested for their ability to proliferate in response to polyclonal activation by immobilized anti-CD3 (10 $\mu$g/ml) and soluble anti- CD28 (1 μg/ml) antibodies or CD3-depleted allogeneic PBMCs (MLR). Proliferation was measured by incorporation of $^3$H-thymidine into de novo synthesized DNA 3 days after initiation of the culture.

IV. Restimulation of Cells for Analysis of Intracellular Cytokine Production

Intracellular cytokines were detected by flow cytometry as described in Sornasse, et al. (1996) *J. Exp. Med.* 184:473–483, with slight modifications. 1–2×10$^6$ T cells/ml were stimulated with immobilized anti-CD3 (10 μg/ml) and soluble anti-CD28 (1 μg/ml; Pharmingen) in complete medium. Upon initiation of the culture, the plates were centrifuged for 5 minutes at 800×g. After 3 hours of activation, brefeldin A (10 μg/ml; Sigma, Milan, Italy) was added. After a total of 6 hours of activation, T cells were collected, washed in PBS and fixed with 2% formaldehyde. After fixation, T cells were permeabilized by incubation in PBS supplemented with 2% FCS and 0.5% Saponin (Sigma). Permeabilized T cells were incubated with PE-labeled anti-hIL-4, anti-hIL-2, or anti-hIL-10, and FITC-coupled anti-hIFN-γ. All antibodies were obtained from Pharmingen. After washing, cells were analyzed using a FACScan® flow cytometer (Beckton Dickenson) and data were analyzed with Celiquest software (Beckton Dickenson). Quadrant markers were positioned to include 95% of stained, unstimulated cells in the lower left square.

V. Proliferatin of Polarized T Cells

CD4$^+$ cord blood T cells were activated by anti-CD3 antibodies cross-linked to CD32$^+$CD80$^+$CD58$^+$ L-cells in the presence of IL-4, IL-12, or IL-10 and IFN-α. Following two rounds of stimulation, T cells were tested for their ability to proliferate in response to immobilized anti-CD3 (10 μg/ml) and soluble anti-CD28 (1 μg/ml) antibodies or CD3-depleted allogeneic PBMCs (MLR).

Polarized T-cell subsets were compared for their proliferative capacity following polyclonal or antigen-specific activation. To analyze proliferation in response to polyclonal activation, 96 well flat-bottom plates (Costar) were coated overnight with anti-CD3 antibodies (10 μg/ml), and washed three times with PBS. T cells were plated at an initial density of 2.5×10$^5$ cells/ml in a final volume of 200 μl of Yssel medium supplemented with 5% human plasma, 100 U/ml penicillin/streptomycin, and soluble anti-CD28 antibodies (1 μg/ml). Control cultures consisted of T cells cultured in the absence of anti-CD3 and anti-CD28 antibodies. To determine proliferation induced by antigen-dependent activation, MLRs were performed. T cells (2.5×10$^5$ cells/ml) were stimulated with irradiated (6000 Rads) allogeneic PBMC (2.5×10$^5$ cells/ml) that had been depleted of CD3$^+$ cells by negative selection. Cells were co-cultured in a final volume of 200 μl of Yssel medium supplemented with 5% human plasma, 100 U/ml penicillin/streptomycin in 96 well round bottom plates (Costar). Neutralizing anti-IL-10 (50 μg/ml) (9D7, DNAX Research Institute) and/or anti-TGFβ$_{2/3}$ (20 μg/ml) (Genzyme, Cambridge, Mass.) antibodies were added as indicated. After 48 hours, wells were pulsed for 16 hours with 1 μCi/well $^3$H-thymidine (Amersham, Uppsala, Sweden). Cells were harvested, and counted in a scintillation counter.

CD4$^+$ cord blood T cells were activated by anti-CD3 antibodies cross-linked on CD32$^+$CD80$^+$CD58$^+$ L-cells in the presence of IL-4, IL-12, or IL-10 and IFN-α, at the end of the primary (day 7) and secondary (day 14) stimulations cells were counted and the fold increase in total cell number was determined. T cells were activated with IL-4, IL-12, or IL-10 in the absence or presence of IFN-α in the primary, secondary, or primary and secondary stimulations. Incorporation of $^3$H-thymidine was assessed 3 days after initiation of the secondary stimulation.

All citations herein are incorporated herein by reference to the same extent as if each individual publication or patent application was specifically and individually indicated to be incorporated by reference.

Many modifications and variations of this invention can be made without departing from its spirit and scope, as will be apparent to those skilled in the art. The specific embodiments described herein are offered by way of example only, and the invention is to be limited by the terms of the appended claims, along with the full scope of equivalents to which such claims are entitled; and the invention is not to be limited by the specific embodiments that have been presented herein by way of example.

What is claimed is:

1. A method to induce differentiation of an isolated or purified naïve CD4$^+$T cell to a Tr1 cell comprising contacting the naïve CD4$^+$T cell with a combination of interferon-α (IFN-α) and IL-10 in an amount effective to induce differentiation.

2. The method of claim 1, wherein said Tr1 cell is characterized by:
 a) CD4 expression;
 b) high levels of IL-10 production;
 c) significant levels of TGF-β or IFN-β production; and
 d) little or no production of IL-4 or IL-2.

3. The method of claim 2, wherein;
 a) the IL-10 production is at least 6000 pg;
 b) the TGF-β production is at least 100 pg;
 c) the IFN-γ production is at least 400 pg;
 d) the IL-4 production is less than 200 pg; or
 e) the IL-2 production is lees than 200 pg;
when evaluated from cultures of about 10$^6$ cells per ml per 48 hours.

4. The method of claim 2, wherein:
 a) the IL-10 production is at least 12000 pg;
 b) the TGF-β production is at least 600 pg;
 c) the IFN-γ production is at least 1000 pg;
 d) the IL-4 production is less than 100 pg; or
 e) the IL-2 production is less than 100 pg;
when evaluated from cultures of about 10$^6$ cells per ml per 48 hours.

5. The method of claim 2, wherein said Tr1 cell:
 a) has a reduced proliferative potential in response to polyclonal activation; and/or
 b) suppresses response to alloantigens by responder T cells.

6. The method of claim 1, wherein said Tr1 cell suppresses antigen-specific activation of a naive autologous T cell.

7. The method of claim 5, wherein said suppressed response to alloantigens is mediated by IL-10 and/or TGF-β.

8. The method of claim 1, wherein said contacting is in combination with an antigen.

9. The method of claim 8, wherein said antigen is an alloantigen.

10. The method of claim 1, wherein said Tr1 cell is further proliferated in IL-15.

11. The method of claim 1, wherein said Tr1 cell is further tested for antigen specificity.

12. A method to induce differentiation of an isolated or purified cord blood T cell to a Tr1 cell comprising contacting the cord blood cell with IFN-α in an amount effective to induce differentiation.

* * * * *